United States Patent
Pusterla et al.

(10) Patent No.: US 6,770,873 B2
(45) Date of Patent: Aug. 3, 2004

(54) METHOD FOR MEASURING TOTAL CONCENTRATION OF CARBON MONOXIDE AND HYDROCARBONS IN OXYGEN BY ION MOBILITY SPECTROMETRY

(75) Inventors: Luca Pusterla, Milan (IT); Marco Succi, Milan (IT)

(73) Assignee: Saes Getters S.p.A., Lainate (IT)

( * ) Notice: Subject to any disclaimer, the term of this patent is extended or adjusted under 35 U.S.C. 154(b) by 0 days.

(21) Appl. No.: 10/454,878

(22) Filed: Jun. 5, 2003

(65) Prior Publication Data

US 2003/0209663 A1 Nov. 13, 2003

Related U.S. Application Data

(63) Continuation of application No. PCT/IT02/00261, filed on Apr. 23, 2002.

(30) Foreign Application Priority Data

May 7, 2001 (IT) ..................................... MI2001A0929

(51) Int. Cl.$^7$ ............................................... H01J 49/40
(52) U.S. Cl. ....................... 250/282; 250/583; 250/288; 250/287
(58) Field of Search ................................ 250/282, 288, 250/287, 283

(56) References Cited

U.S. PATENT DOCUMENTS

| | | |
|---|---|---|
| 3,787,333 A | 1/1974 | Ichihara et al. |
| 4,777,363 A | 10/1988 | Eiceman et al. |
| 5,457,316 A | 10/1995 | Cohen et al. |
| 5,955,886 A | 9/1999 | Cohen et al. |

FOREIGN PATENT DOCUMENTS

| | | |
|---|---|---|
| EP | 0 453 190 A2 | 10/1991 |
| EP | 0 902 283 A1 | 3/1999 |

*Primary Examiner*—John R. Lee
*Assistant Examiner*—James J. Leybourne
(74) *Attorney, Agent, or Firm*—Akin Gump Strauss Hauer & Feld, L.L.P.

(57) ABSTRACT

A method is provided for the quantitative analysis by ion mobility spectrometry of the concentration of carbon monoxide, methane and higher hydrocarbon species in an oxygen stream. The method includes converting these species present in the oxygen stream into carbon dioxide, measuring the concentration of the carbon dioxide, and deducing from this measurement the initial concentration of the oxidizable species.

10 Claims, 1 Drawing Sheet

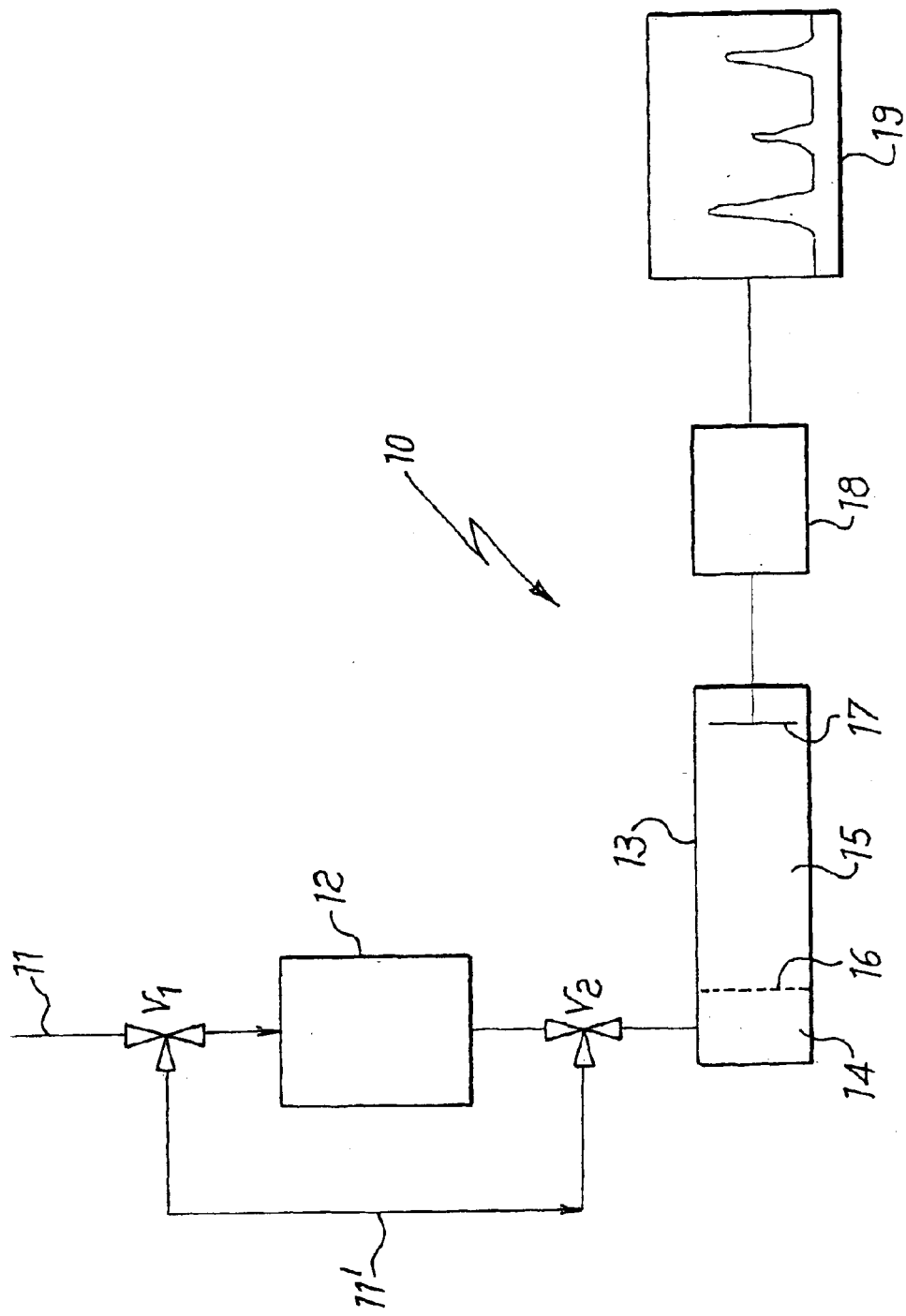

METHOD FOR MEASURING TOTAL CONCENTRATION OF CARBON MONOXIDE AND HYDROCARBONS IN OXYGEN BY ION MOBILITY SPECTROMETRY

CROSS-REFERENCE TO RELATED APPLICATIONS

This application is a continuation of International Application No. PCT/IT02/00261, filed Apr. 23, 2002, which was published in the English language on Nov. 14, 2002, under International Publication No. WO 02/090959 A1, the disclosure of which is incorporated herein by reference.

BACKGROUND OF THE INVENTION

The present invention relates to a method for measuring the total concentration of carbon monoxide and hydrocarbons in oxygen by ion mobility spectrometry.

Oxygen is widely employed as a reacting gas in the integrated circuit industry, in order to build up oxide layers generally acting as an electric insulation between different active portions of a circuit. As is known, in the manufacture of these devices, the purity of all the used materials has a basic importance. As a matter of fact, contaminants possibly present in the reactants or in the reaction environment may be incorporated into the solid state devices, thus altering their electrical features and giving rise to production wastes. The purity specification of the gases employed in the manufacturing process may change among different manufacturers and depending on the specific process the gas is employed in. Generally, a gas is considered to be acceptable for manufacturing purposes when its impurities content does not exceed 10 ppb (parts per billion, namely an impurity molecule per $10^9$ total gas molecules). Preferably, the impurities content is lower than 1 ppb. It thus becomes important to have the possibility to measure extremely low concentrations of impurities in the gases in an accurate and reproducible way.

A technique that can be exploited for such purpose is ion mobility spectrometry, known in the art under the abbreviation IMS. The same abbreviation is also used for the instrument the technique is performed with, indicating in this case "Ion Mobility Spectrometer". The interest in such a technique comes from its extremely high sensitivity, associated with limited size and cost of the instrument. By operating under suitable conditions, it is possible to detect species in a gas medium, in the gas or vapor phase, in amounts of the order of picograms (pg, namely $10^{-12}$ g) or in concentrations of the order of parts per trillion (ppt, equivalent to one molecule of analyzed substance per $10^{12}$ molecules of sample gas). IMS instruments and analytical methods in which they are employed are disclosed, for instance, in U.S. Pat. Nos. 5,457,316 and 5,955,886, assigned to the U.S. firm PCP, Inc.

The physicochemical basis of the technique is very complicated, just as the interpretation of the IMS analytical results. For an explanation of this basis and results, reference can be made to the book G. A. Eiceman and Z. Karpas, *Ion Mobility Spectrometry*, CRC Press (1994).

Briefly, an IMS instrument essentially consists of a reaction zone, a separation zone and a charged particle collector.

Within the reaction zone there occurs the ionization of the sample, comprising gases or vapors to be analyzed in a carrier gas, usually by β-radiation emitted by $^{63}Ni$. The ionization mainly occurs on the carrier gas, with the formation of so-called "reactant ions," whose charge is then distributed to the species present depending on their electron or proton affinities or on their ionization potentials.

The reaction zone is divided from the separation zone by a grid which, when maintained at a suitable potential, prevents the ions produced in the reaction zone from entering into the separation zone. The analysis "time zero" is established by the moment when the grid potential is annulled, thus allowing the ions admission into the separation zone.

The separation zone comprises a series of electrodes, which create such an electric field that the ions are carried from the grid toward the collector. In this zone, maintained at atmospheric pressure, a gas stream is present having an opposite flow direction with respect to the direction of the ion movement. The counter-flow gas (defined in the field as "drift gas") is an extremely pure gas, which may either correspond to the gas whose impurities content is to be determined, or may be a different gas. The motion velocity of the ions depends on the electric field and on the cross-section of the same ions in the gaseous medium, so that different ions take different times for crossing the separation zone and reaching the particle collector. The time elapsed from "time zero" to the time of arrival on the particle collector is called "time of flight." The collector is connected to the signal processing system, which transforms the current values sensed as a function of time into the final graph, where peaks corresponding to the different ions are shown as a function of the "time of flight." From the determination of this time and the knowledge of the test conditions, it is possible to trace the presence of the substances which are the object of the analysis, whereas from the peak areas it is possible to calculate, through suitable computation algorithms, the concentration of the corresponding species.

In the most common mode, an IMS analysis is carried out on species having a positive charge. In the case of oxygen, in contrast, oxygen forms negative species in the reaction zone. Under such conditions in the IMS analysis (negative mode) only species can be sensed having electron affinity higher than oxygen and then being able to receive a charge from this gas. This essentially occurs in the case of carbon dioxide ($CO_2$). The analysis of impurities in oxygen is therefore limited. Among the species whose concentration in oxygen is interesting to measure, there are for instance carbon monoxide (CO) and hydrocarbons, particularly methane ($CH_4$).

BRIEF SUMMARY OF THE INVENTION

An object of the present invention is to provide a method of measuring the total concentration of CO and hydrocarbons in oxygen by ion mobility spectrometry.

According to a first embodiment of the present invention, this object is reached through a method comprising the following steps:

a) converting carbon monoxide and hydrocarbons, present in the oxygen stream, into carbon dioxide;

b) measuring the concentration of carbon dioxide in the oxygen after the conversion according to step a); and c) deducing from the measurement of step b) the total initial concentration of carbon monoxide and hydrocarbons.

According to a second embodiment of the invention, the method is employed in the case of oxygen initially already containing carbon dioxide as an impurity (such condition can be ascertained through a preliminary indicative test performed on oxygen without previously submitting the same to the conversion step of CO and hydrocarbons). In this case, a concentration value will be obtained in the IMS analysis corresponding to the sum of the originally present $CO_2$ and that coming from the conversion of CO and hydrocarbons. In this case, a variation of the method of the invention is employed comprising the following steps:

a) converting carbon monoxide and hydrocarbons, present in the oxygen stream, into carbon dioxide;

b) measuring the concentration of carbon dioxide in the oxygen stream after the conversion according to step a);

b') performing a further measurement of carbon dioxide concentration in the oxygen stream not submitted to the conversion step according to step a); and c) deducing from the comparison of the carbon dioxide concentrations measured in steps b) and b') the initial concentration of carbon monoxide and hydrocarbons.

BRIEF DESCRIPTION OF THE SEVERAL VIEWS OF THE DRAWINGS

The foregoing summary, as well as the following detailed description of the invention, will be better understood when read in conjunction with the appended drawing. For the purpose of illustrating the invention, there is shown in the drawing an embodiment which is presently preferred. It should be understood, however, that the invention is not limited to the precise arrangements and instrumentalities shown. In the drawing:

The sole FIGURE is a schematic flow diagram showing a system for practically carrying out the method of the invention.

DETAILED DESCRIPTION OF THE INVENTION

According to the method of the invention, CO and hydrocarbons, which are species not detectable in oxygen by a standard IMS analysis, are quantitatively transformed into carbon dioxide ($CO_2$), which in contrast is a measurable species in this analysis.

The method of the invention may be put into practice by using the gas treatment system schematically shown in the drawing. System 10 comprises an inlet line 11 for the gas under examination. Along line 11 a converter 12 is arranged for converting CO and hydrocarbons into $CO_2$. System 10 further comprises, upstream and downstream of converter 12, two three-way valves $V_1$ and $V_2$, that allow the insulation of converter 12 from the gas stream, diverting the latter along secondary line 11'. Downstream of converter 12 or line 11' the IMS analyzer 13 is present, which consists of the reaction zone 14, divided from the separation zone 15 by grid 16. At the end of zone 15 opposite from zone 14, a particle collector 17 is arranged. No further details of the analyzer 13, such as inlet and outlet openings for the "drift gas," are shown. The collector is electrically connected to unit 18, comprising an electronic section for the transformation of electrical pulses from collector 17 into numerical data and a computation section (for example a microprocessor) for processing these data. Unit 18 may be physically integrated into a single body with the IMS instrument. Finally, unit 18 produces as an analysis result spectrum 19, where peaks are recorded corresponding to the different chemical species sensed as a function of their time of flight in instrument 13.

In the first embodiment of the method according to the invention, the entire oxygen stream entering system 10 is sent to converter 12 by suitably operating valves $V_1$ and $V_2$, the conversion of CO and hydrocarbons is carried out, and the thus-treated gas is sent to IMS analyzer 13 in order to carry out the analysis.

In the second embodiment of the method according to the invention, step b) is carried out as in the case of the first embodiment, while step b') is carried out by sending the entire oxygen stream entering system 10 to the analyzer 13 through line 11', insulating converter 12 by suitably operating valves $V_1$ and $V_2$ in this case too.

Converter 12 for the conversion of CO and hydrocarbons to $CO_2$ comprises at least one oxidation catalyst compound. Continuous regeneration of such a compound is favored in that CO and hydrocarbons are present as traces in an atmosphere nearly completely consisting of oxygen. Catalyst compounds useful for this conversion are, for instance, the oxides of some noble metals, such as ruthenium, rhodium, palladium and platinum. Among these, palladium oxide (PdO) is preferred. The optimal working temperature of PdO is between about 200° C. and about 350° C. Palladium oxide or even complete converters for the conversion of CO and hydrocarbons containing this compound are commercially available and sold, for instance, by the Italian firm SAES Getters S.p.A., by the German firm Degussa-Hüls AG, and by the U.S. firm Engelhard Co.

We claim:

1. A method for measuring a total concentration of carbon monoxide and/or hydrocarbons in an oxygen stream to be examined by ion mobility spectrometry, comprising the following steps:

(a) converting any carbon monoxide and hydrocarbons present in the oxygen stream to carbon dioxide;

(b) measuring a concentration of carbon dioxide in the oxygen stream after converting step a); and (c) deducing from measuring step b) the total initial concentration of carbon monoxide and/or hydrocarbons in the oxygen stream.

2. The method according to claim 1, employing a gas treatment system (10) comprising an inlet line (11) for the oxygen stream to be examined, a converter (12) for converting carbon monoxide and hydrocarbons in the oxygen stream, two three-way valves ($V_1$; $V_2$) arranged upstream and downstream of the converter (12), an IMS analyzer (13) for measuring the concentration of carbon dioxide, and a sensing and data processing unit (18) for deducing the concentration of carbon monoxide and/or hydrocarbons from the concentration of carbon dioxide, wherein the converting step (a) is carried out by operating the two three-way valves ($V_1$; $V_2$) to send the entire oxygen stream entering the treatment system (10) to the converter (12).

3. The method according to claim 2, wherein the converter (12) comprises at least one catalyst compound which is active in hydrocarbon oxidation and comprises a noble metal oxide.

4. The method according to claim 3, wherein the catalyst compound comprises palladium oxide.

5. The method according to claim 4, wherein during step (b) the palladium oxide is maintained at a temperature between about 200° C. and about 350° C.

6. The method according to claim 1, further comprising a step:

(b') measuring an initial carbon dioxide concentration in the oxygen stream not submitted to converting step (a), and wherein step (c) is performed by comparing the carbon dioxide concentrations measured in steps (b) and (b').

7. The method according to claim 6, employing a gas treatment system (10) comprising an inlet line (11) for the oxygen stream to be examined, a converter (12) for converting carbon monoxide and hydrocarbons in the oxygen stream, two three-way valves ($V_1$; $V_2$) arranged upstream and downstream of the converter (12), an IMS analyzer (13) for measuring the concentration of carbon dioxide, and a sensing and data processing unit (18) for deducing the concentration of carbon monoxide and/or hydrocarbons from the concentration of carbon dioxide, wherein the measuring step (b') is carried out by operating the two three-way valves ($V_1$; $V_2$) to send the entire oxygen stream entering the treatment system (10) to the IMS analyzer (13) through a secondary line (11') avoiding passage of the stream through the converter (12).

8. The method according to claim 7, wherein the converter (12) comprises at least one catalyst compound which is active in hydrocarbon oxidation and comprises a noble metal oxide.

9. The method according to claim 8, wherein the catalyst compound comprises palladium oxide.

10. The method according to claim 9, wherein during step (b) the palladium oxide is maintained at a temperature between about 200° C. and about 350° C.

* * * * *